United States Patent [19]

Arkles

[11] Patent Number: 4,469,881
[45] Date of Patent: Sep. 4, 1984

[54] [2-(p-t-BUTYLPHENYL)ETHYL]SILANES AND METHOD OF MAKING THE SAME

[75] Inventor: Barry C. Arkles, Oreland, Pa.

[73] Assignee: Petrarch Systems Inc., Bristol, Pa.

[21] Appl. No.: 424,783

[22] Filed: Sep. 27, 1982

[51] Int. Cl.$^3$ .......................... C07F 7/08; C07F 7/10; C07F 7/18

[52] U.S. Cl. .................................... 556/453; 556/410; 556/452; 556/457; 556/479; 556/482; 556/484; 556/489; 548/110

[58] Field of Search ................ 548/110; 556/482, 484, 556/489, 479, 410, 457, 482, 453

[56] References Cited

U.S. PATENT DOCUMENTS 2,698,333  12/1954  Cole et al. .................. 556/489 X
4,242,272  12/1980  Koga et al. .................. 556/489
4,269,993   5/1981  Ohtake et al. ................ 556/489 X

OTHER PUBLICATIONS

Corey and Venkateswarlu, *J. Am. Chem. Soc.* 94: 6190, (1962).
"Chemical Synthesis and Cloning of Tyrosine t-RNA Gene", *Meth. in Enzymology,* 68:109, (1978).

*Primary Examiner*—Paul F. Shaver
*Attorney, Agent, or Firm*—Panitch, Schwarze, Jacobs & Nadel

[57] ABSTRACT

[2-(p-t-Butylphenyl)ethyl]silanes are provided having the general formula:

$$Si(B)_x(R)_y(A)_z$$

wherein B is a (p-t-butylphenyl)ethyl moiety, R is an alkyl or aryl moiety and A is a hydrolyzeable moiety; x equals 1 or 2, y equals 0, 1 or 2 and z equals 1, 2 or 3 such that x plus y plus z equals 4. The bulky substituted silanes are produced by the hydrosilylation of p-t-butylstyrene.

[2-(p-t-Butylphenyl)ethyl] substituted disiloxanes are also provided, having the general formula:

$$(B)_x(R)_y(A)_zSi-O-Si(A)_z(R)_y(B)_x$$

wherein B, R, A, x, y and z are as defined above except that z equals 0,1 or 2 and x plus y plus z equals 3. The bulky substituted disiloxanes are produced by the hydrolysis of above-described bulky substituted silanes.

11 Claims, No Drawings

[2-(p-t-BUTYLPHENYL)ETHYL]SILANES AND METHOD OF MAKING THE SAME

BACKGROUND OF THE INVENTION

The present invention is directed towards silanes and disiloxanes with the bulky, (p-t-butylphenyl)ethyl substituent. The compounds of the present invention are useful as protecting groups in the synthesis of biological macromolecules.

Silylation with bulky groups is important in the production of many biological macromolecules. Bulky silane groups are used to protect certain functional groups during intermediate steps in the synthesis of these molecules and to sterically control other synthetic steps. For example, the t-butyldimethylsilyl protecting group was used in prostaglandin synthesis by Corey and Venkateswarlu, J.Am.Chem. Soc. 94: 6190, (1962). The t-butyldiphenylsilyl group was used by Brown et al in the synthesis of transfer riboneucleic acid in "Chemical Synthesis And Cloning Of Tyrosine t-RNA Gene", *Meth. In Enzymology,* 68:109 (1978).

The use of bulky silyl groups, in contrast to older methods in which simple trimethylsilyl groups are used, is related to the increased ability of such compounds to sterically control intermediate synthetic steps and the increased resistance of such groups to hydrolysis. Presently, t-butylsilyl protecting groups are used for this purpose.

Currently, processes for introducing t-butyl groups are generally expensive and awkward. These processes involve the reaction of t-butyl lithium with a chlorosilane in the following manner:

$$(CH_3)_3CLi + (CH_3)_2SiCl_2 \rightarrow (CH_3)_3C(CH_3)_2SiCl + LiCl$$

It is the object of this invention to provide bulky silane groups, having increased ability to sterically control synthetic steps and increased stability. It is a further object of this invention to provide an easier and less expensive method of producing such compounds.

BRIEF SUMMARY OF THE INVENTION

The novel compounds of the present invention comprise: [2-(p-t-butylphenyl)ethyl]silanes having the general formula:

$$Si(B)_x(R)_y(A)_z$$

wherein B is a (p-t-butylphenyl)ethyl moiety, R is an alkyl or aryl moiety and A is a hydrolyzable moiety; x equals 1 or 2, y equals 0, 1 or 2 and z equals 1, 2 or 3 such that x plus y plus z equals 4. The bulky substituted silanes are produced by the hydrosilylation of p-t-butylstyrene.

The present invention also includes novel [2-(p-t-butylphenyl)ethyl] substituted disiloxanes having the general formula:

$$(B)_x(R)_y(A)_zSi-O-Si(A)_z(R)_y(B)_x$$

wherein B, R, A, x, y and z are as defined above except that z equals 0, 1 or 2 and x plus y plus z equals 3. Substituted disiloxanes are produced by the hydrolysis of the above described bulky substituted silanes.

The novel silanes of the invention have superior thermal stability and resistance to hydrolysis, as compared to previously known compounds. The silanes are especially useful in sterically controlling intermediate synthetic steps in the synthesis of biological macromolecules.

DETAILED DESCRIPTION OF THE PREFERRED EMBODIMENTS

The novel compounds of the present invention may be produced by the reaction of p-t-butylstyrene and a silane. This hydrosilylation reaction results in the opening of one of the bonds between the double-bonded alpha and beta carbon atoms in the p-t-butylstyrene molecule, and the formation of a single bond between the beta carbon and the silicon atom.

The hydrosilylation reaction may be represented as follows:

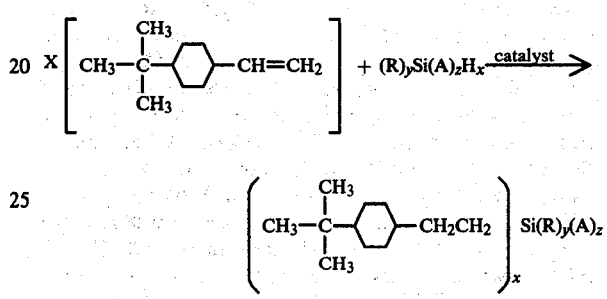

wherein R is an alkyl or aryl moiety, A is a hydrolyzable group, x is 1 or 2, y is 0, 1 or 2 and z is 1, 2, or 3 such that x+y+z=4. If necessary, or desired, other chemical transformations may be performed on the resulting bulky substituted silane after the hydrosilylation.

Various [2-(p-t-butylphenyl)ethyl]silanes may be obtained by altering the substituents present on the silane which is used to hydrosilylate the p-t-butylstyrene molecule. Such substituents (R) may include alkyl or aryl groups. Preferably, the alkyl groups used are lower alkyls, such as methyl, ethyl, propyl, or butyl groups. The aryl groups used are preferably phenyl or tolyl groups.

The novel compounds of the present invention contain at least one hydrolyzable moiety to facilitate their use as protective groups in biosynthetic reactions. The hydrolyzable group(s) serve(s) as point(s) of attachment to various biological macromolecules. Typically, these hydrolyzable groups (A) may be halogens, dimethylamines, imidazoles or alkoxy groups.

The hydrosilylation reaction requires the presence of a catalyst. Typically, a platinum catalyst is employed. Preferably the catalyst bis(benzonitrile) platinum II chloride is used to catalyze this reaction, but other suitable platinum catalysts will be obvious to those skilled in the art of silane chemistry. The reaction may be carried out at low heat and, if necessary low pressure, such as autogenous pressure. The bulky substituted silane may be recovered by vacuum distillation.

The silanes produced by the hydrosilylation of the p-t-butylstyrene molecule may be modified by simple hydrolysis to produce disiloxanes. This hydrolysis can be accomplished by allowing the [2-(p-t butylphenyl)ethyl]silane to react with water. The reaction is spontaneous and may be initiated by dissolving the silane in a solvent, such as tetrahydrofuran, and then adding the solution to water.

Where the disiloxane has two hydrolyzable groups, i.e. where z=1, such as in the compound di[2-(p-t-butylphenyl)ethyl]dichlorodimethyldisiloxane, the disiloxane may be used in the same manner as the novel silanes of the invention to provide thermal stability, resistance to hydrolysis and steric control of intermediate steps in the synthesis of biological macromolecules, except that there may be a double attachment of the disiloxane to the macromolecule, i.e. at each hydrolyzable group site. Where the disiloxane has no hydrolyzable groups, as in the compound of Example 3 below, the disiloxane may be used as an endcapper for silicon polymers.

The novel compounds of the present invention will now be illustrated in more detail with reference to the following specific, non-limiting examples:

EXAMPLE 1

A 3 neck 5 liter flask, equipped with a dry ice/acetone condenser, addition funnel, thermometer and magnetic stirrer was charged with 10 moles of dimethylchlorosilane (1,113 mls), 500 mls of toluene, 200 mls of t-butylstyrene and approximately 0.2 g of bis(benzonitrile) platinum II chloride. The mixture was heated until the initiation of the hydrosilylation reaction was indicated by a sharp exotherm. The balance of the 10 moles of t-butylstyrene was added at a rate to maintain the temperature of the reaction vessel below 80° C. The mixture was then heated to maintain a temperature of 80° C. after the addition was complete. The mixture was then distilled under vacuum. The fraction boiling at 120°-124° C. at 2 mm Hg was identified as [2-(p-t-butylphenyl)ethyl]dimethylchlorosilane by Infra-Red Spectroscopy (IR) and Nuclear Magnetic Resonance Spectroscopy (NMR). The reaction yield was 95% of the theoretical maximum.

EXAMPLE 2

A 3 liter, 10,000 PSI autoclave was cooled to −40° to −30° C. by immersion in dry ice/acetone. The autoclave was charged with 250 mls of toluene, 202 gm of dichlorosilane, 320 gm of p-t-butylstyrene, 1 gm of di-t-butyl (p-hydroxy)toluene [BHT] and 0.1 gm of bis(benzonitrile) platinum II chloride. The autoclave was heated over six hours to a temperature of 100° C. and held at that temperature for 2 hours at autogenous pressure. Vacuum distillation of the reaction product gave a fraction which boiled at 175°-180° C. at 1 mm Hg which was identified as di[2-(p-t-butylphenyl)ethyl]dichlorosilane by IR and NMR. This reaction yielded 32% of the theoretical maximum.

EXAMPLE 3

[2-(p-t-butylphenyl)ethyl]dimethylchlorosilane (as obtained in Example 1) was dissolved in an equal volume of tetrahydrofuran and added to 5 volumes of water and stirred for one week. The reaction product was isolated as a solid fraction having a melting point of 72°-74° C. and a boiling point of 233°-240° C. at 1 mm Hg. The reaction yielded 96% of the theoretical maximum.

The present invention may be embodied in other specific forms without departing from the spirit of essential attributes thereof and, accordingly, reference should be made to the appended claims, rather than to the foregoing specification as indicating the scope of the invention.

I claim:

1. [2-(p-t-butylphenyl)ethyl]silanes of the general formula

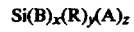

wherein B is a 2-(p-t-butylphenyl)ethyl group, R is an organic substituent selected from the group consisting of aryl and alkyl groups, A is a hydrolyzable moiety, and where x equals 1 or 2, y equals 0, 1 or 2 and z equals 1, 2 or 3 such that x plus y plus z equals 4.

2. The compound of the general formula of claim 1 where R is an organic substituent selected from the group consisting of phenyl, tolyl, and lower alkyl groups and A is a hydrolyzable moiety selected from the group consisting of halogen, dimethylamine, imidazole and alkoxy groups.

3. The compound of the general formula of claim 1 where R is lower alkyl and A is halogen.

4. [2-(p-t-butylphenyl)ethyl]dimethylchlorosilane.

5. di[2-(p-t-butylphenyl)ethyl]dichlorosilane.

6. di[2-(p-t-butylphenyl)ethyl]tetramethyldisiloxane.

7. A bulky substituted disiloxane of the general formula:

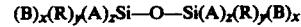

wherein B is a 2-(p-t-butylphenyl)ethyl group, R is an organic substituent selected from the group consisting of aryl and alkyl groups, A is a hydrolyzable moiety, and where x equals 1 or 2, y equals 0, 1 or 2 and z equals 0, 1 or 2 such that x plus y plus z equals 3.

8. A compound of claim 7 where R is selected from the group of organic substituents consisting of methyl, ethyl, propyl, butyl, phenyl and tolyl groups and A is selected from the group of hydrolyzable moieties consisting of halogen, dimethylamine, imidazole and alkoxy groups.

9. A method of manufacturing [2-(p-t-butylphenyl)ethyl]silanes comprising the hydrosilylation of p-t-butylstyrene with a substituted silane having the general formula:

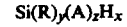

wherein R is an organic substituent selected from the group consisting of aryl and alkyl groups, A is a hydrolyzable moiety, x equals 1 or 2, y equals 0, 1 or 2 and z equals 1, 2 or 3 such that x+y+z=4, said hydrosilylation reaction being carried out in the presence of a bis(benzonitrile) platinum II chloride catalyst.

10. A method according to claim 9 wherein R is an organic substituent selected from the group consisting of phenyl, tolyl and lower alkyl and the hydrolyzable moiety is selected from the group consisting of halogen, dimethylamine, imidazole and alkoxy.

11. A method according to claim 9 wherein R is lower alkyl and A is halogen.

* * * * *